US 12,023,120 B2

(12) United States Patent
Dong et al.

(10) Patent No.: US 12,023,120 B2
(45) Date of Patent: Jul. 2, 2024

(54) FLUID POWERED MASTER-SLAVE ACTUATION FOR MRI-GUIDED INTERVENTIONS

(71) Applicant: VERSITECH LIMITED, Hong Kong (CN)

(72) Inventors: Ziyang Dong, Hong Kong (CN); Ka Wai Kwok, Hong Kong (CN); Ziyan Guo, Hong Kong (CN); Kit Hang Brian Lee, Hong Kong (CN)

(73) Assignee: VERSITECH LIMITED, Hong Kong (CN)

( * ) Notice: Subject to any disclaimer, the term of this patent is extended or adjusted under 35 U.S.C. 154(b) by 968 days.

(21) Appl. No.: 16/969,926

(22) PCT Filed: Mar. 8, 2019

(86) PCT No.: PCT/IB2019/051877
§ 371 (c)(1),
(2) Date: Aug. 13, 2020

(87) PCT Pub. No.: WO2019/171336
PCT Pub. Date: Sep. 12, 2019

(65) Prior Publication Data
US 2021/0007817 A1   Jan. 14, 2021

Related U.S. Application Data

(60) Provisional application No. 62/640,302, filed on Mar. 8, 2018.

(51) Int. Cl.
*A61B 34/37* (2016.01)
*F15B 15/06* (2006.01)
(Continued)

(52) U.S. Cl.
CPC .............. *A61B 34/37* (2016.02); *F15B 15/06* (2013.01); *F15B 15/1423* (2013.01);
(Continued)

(58) Field of Classification Search
CPC ............ A61B 34/37; A61B 2034/2051; A61B 2090/031; A61B 2090/374;
(Continued)

(56) References Cited

U.S. PATENT DOCUMENTS 4,070,946 A    1/1978  Sandvik et al.
2008/0245985 A1*  10/2008  Heim .................. F16K 99/0049
                                              251/129.06
(Continued)

FOREIGN PATENT DOCUMENTS

| CN | 103370023 A | 10/2013 |
| CN | 104042344 A | 9/2014 |
| EP | 3175813 A1 | 6/2017 |

OTHER PUBLICATIONS

ASTM. (2006) Designation: F2119-07, Standard Test Method for Evaluation of MR Image Artifacts from Passive Implants, West Conshohocken, PA: American Society for Testing and Materials (ASTM) International, 4 pages.
(Continued)

*Primary Examiner* — Baisakhi Roy
*Assistant Examiner* — Kaitlyn E Sebastian
(74) *Attorney, Agent, or Firm* — Leason Ellis LLP

(57) ABSTRACT

Systems and methods for an effective solution to MR safe actuation in all MRI-guided (robot-assisted) procedures are provided. The present integrated hydraulic transmission method or system uses piston-based cylinders (101,102,201, 308(C1), 309(C2), 310(C3), 402, 501) to provide continuous bi-lateral rotation with unlimited range in an MRI environment. Positional and torque control can also be achieved.
(Continued)

The system includes a master unit and a slave unit each comprising: a plurality of cylinders (101,102,201,308(C1), 309(C2), 310(C3), 402, 501), a piston (105,301,302,303, 401,502) inserted within the bottom surface of each cylinder (101,102,201,308(C1), 309(C2), 310(C3), 402, 501), a seal positioned with each cylinder (101,102,201,308(C1), 309 (C2), 310(C3), 402, 501) between the piston (105,301,302, 303,401,502) and the top surface of the cylinder (101,102, 201,308(C1), 309(C2), 310(C3), 402, 501) to inhibit a fluid from passing across the seal, and a plurality of tubes (103) connecting the master unit cylinders and slave unit cylinders (402).

20 Claims, 10 Drawing Sheets

(51) Int. Cl.
  *F15B 15/14* (2006.01)
  *A61B 34/20* (2016.01)
  *A61B 90/00* (2016.01)
(52) U.S. Cl.
  CPC .. *F15B 15/1452* (2013.01); *A61B 2034/2051* (2016.02); *A61B 2090/031* (2016.02); *A61B 2090/374* (2016.02)
(58) Field of Classification Search
  CPC .......... A61B 2017/00535; A61B 34/35; A61B 2090/066; A61B 2017/22051; A61B 2090/401; F15B 15/06; F15B 15/1423; F15B 15/1452; G01R 33/28
  See application file for complete search history.

(56) References Cited

U.S. PATENT DOCUMENTS

2015/0240958 A1* 8/2015 Mosadegh ................ F16K 7/20
                                                                   137/12
2017/0367776 A1* 12/2017 Kwok ...................... A61B 34/35

OTHER PUBLICATIONS

ASTM. (2013) Designation: F2503-13, Standard Practice for Marking Medical Devices and Other Items for Safety in the Magnetic Resonance Environment, West Conshohocken, PA: American Society for Testing and Materials (ASTM) International, 9 pages.
Blanco Sequeiros R, Ojala R, Kariniemi J, Perala J, Niinimaki J, Reinikainen H and Tervonen O. (2005) MR-guided interventional procedures: a review, Acta Radiologica 46: pp. 576-586.
Burkhard N, Frishman S, Gruebele A, Whitney JP, Goldman R, Daniel B and Cutkosky M. (2017) A rolling-diaphragm hydrostatic transmission for remote MR-guided needle insertion, IEEE International Conference on Robotics and Automation 2017, pp. 1148-1153.
Chen Y, Kwok K-W, Ge J, Hu Y, Fok M, Nilsson KR and Tse ZTH. (2014a) Augmented reality for improving catheterization in magnetic resonance imaging-guided cardiac electrophysiology therapy, Journal of Medical Devices, Jun. 2014, vol. 8: pp. 020917-1.
Chen Y, Kwok K-W and Tse ZTH. (2014b) An MR-conditional high-torque pneumatic stepper motor for MRI-guided and robot-assisted intervention, Annals of biomedical engineering 42: pp. 1823-1833.
Cheung CL, Lee K-H, Guo Z, Dong Z, Leong MCW, Lee APW, Kwok K-W and Chen Y. (2016) Kinematic-model-free positional control for robot-assisted cardiac catheterization, Proceedings of The Hamlyn Symposium on Medical Robotics, pp. 80-81.
Chinzei K, Hata N, Jolesz FA and Kikinis R. (2000) MR compatible surgical assist robot: System integration and preliminary feasibility study. MICCAI, pp. 921-933.
Comber DB, Pitt EB, Gilbert HB, Powelson MW, Matijevich E, Neimat JS, Webster III RJ and Barth EJ. (2017) Optimization of curvilinear needle trajectories for transforamenal hippocampotomy, Operative Neurosurgery 13: pp. 15-22.
Comber DB, Slightam JE, Gervasi VR, Neimat JS and Barth EJ. (2016) Design, additive manufacture, and control of a pneumatic MR-compatible needle driver, IEEE Transactions on Robotics 32: No. 1 pp. 138-149.
Feng Y, Guo Z, Dong Z, Zhou X-Y, Kwok K-W, Ernst S and Lee S-L. (2017) An efficient cardiac mapping strategy for radiofrequency catheter ablation with active learning, International Journal of Computer Assisted Radiology and Surgery: 12: pp. 1100-1207.
Fox RW, McDonald AT and Pritchard PJ. (1998) Introduction to fluid mechanics, New York: John Wiley & Sons, 899 pages.
Fritz J, Thomas C, Clasen S, Claussen CD, Lewin JS and Pereira PL. (2009) Freehand real-time MRI-guided lumbar spinal injection procedures at 1.5 T: feasibility, accuracy, and safety. American Journal of Roentgenology 192: pp. W161-W167.
Ganesh G, Gassert R, Burdet E and Bleuler H. (2004) Dynamics and control of an MRI compatible master-slave system with hydrostatic transmission. IEEE International Conference on Robotics and Automation 2004, pp. 1288-1294.
Groenhuis V, Siepel FJ, Veltman J and Stramigioli S. (2017) Design and characterization of Stormram 4: an MRI-compatible robotic system for breast biopsy. IEEE/RS J International Conference on Intelligent Robots and Systems, 6 pages.
Groenhuis V, Veltman J, Siepel FJ and Stramigioli S. (2017) Stormram 3. IEEE Robotics & Automation Magazine 1070.
Guo Z, Dong Z, Lee K-H, Cheung CL, Fu H-C, Ho JDL, He H, Poon W-S, Chan DTM and Kwok K-W. (2018) Compact Design of a Hydraulic Driving Robot for Intra operative MRI-guided Bilateral Stereotactic Neurosurgery IEEE Robotics and Automation Letters, vol. 3, No. 3, pp. 2515-2522.
Guo Z, Lun TTL, Chen Y, Su H, Chan DTM and Kwok K-W. (2016) Novel design of an MR-safe pneumatic stepper motor for MRI-guided robotic interventions. Proceedings of The Hamlyn Symposium on Medical Robotics, pp. 50-51.
Helbich T, Rudas M, Haitel A, Kohlberger P, Thurnher M, Gnant M, Wunderbaldinger P, Wolf G and Mostbeck G. (1998) Evaluation of needle size for breast biopsy: comparison of 14-, 16-, and 18-gauge biopsy needles. AJR. American journal of roentgenology 171 : pp. 59-63.
Kahn T and Busse H. (2012) Interventional magnetic resonance imaging: Springer.
Kinoshita M, McDannold N, Jolesz FA and Hynynen K. (2006) Targeted delivery of antibodies through the blood-brain barrier by MRI-guided focused ultrasound. Biochemical and biophysical research communications 340: pp. 1085-1090.
Kwok K-W, Chow GC, Chau TC, Chen Y, Zhang SH, Luk W, Schmidt EJ and Zion TT. (2014) FPGA-based acceleration of MRI registration: an enabling technique for improving MRI-guided cardiac therapy. Journal of Cardiovascular Magnetic Resonance 16: W11, 3 pages.
Kwok K-W, Lee K-H, Chen Y, Wang W, Hu Y, Chow G, Zhang S, Stevenson W, Kwong R and Luk W. (2014b) Interfacing Fast Multi-phase Cardiac Image Registration with MRI-based Catheter Tracking for MRI-guided Electrophysiological Ablative Procedures. Circulation 130: A18568.
LaRiviere MJ and Gross RE. (2016) Stereotactic Laser Ablation for Medically Intractable Epilepsy: The Next Generation of Minimally Invasive Epilepsy Surgery. Frontiers in surgery, vol. 3, Article 64, pp. 1-16.
Lee K-H, Fu DKC, Guo Z, Dong Z, Leong MCW, Cheung C-L, Lee APW, Luk W and Kwok K-W. (2018) MR Safe Robotic Manipulator for MRI-guided Intra-cardiac Catheterization. IEEE/ASME Transactions on Mechatronics (Accepted), pp. 1-9.
Mortensen J, Talbot S and Burkart JA. (1990) Cross-sectional internal diameters of human cervical and femoral blood vessels: Relationship to subject's sex, age, body size. The Anatomical Record 225: pp. 115-124.

(56) References Cited

OTHER PUBLICATIONS

Pondman KM, Fiitterer JJ, ten Haken B, Kool LJS, Witjes JA, Hambrock T, Macura KJ and Barentsz JO. (2008) MR-guided biopsy of the prostate: an overview of techniques and a systematic review. European urology 54: pp. 517-527.
Prince M, Novelline R, Athanasoulis C and Simon M. (1983) The diameter of the inferior vena cava and its implications for the use of vena caval filters. Radiology 149: pp. 687-689.
Rafii-Tari H, Payne CJ and Yang G-Z. (2014) Current and emerging robot-assisted endovascular catheterization technologies: a review. Annals of biomedical engineering 42: pp. 697-715.
Rahmathulla G, Recinos PF, Kamian K, Mohammadi AM, Ahluwalia MS and Barnett GH. (2014) MRI-guided laser interstitial thermal therapy in neuro-oncology: a review of its current clinical applications. Oncology 87: pp. 67-82.
Song S-E, Cho NB, Fischer G, Hata N, Tempany C, Fichtinger G and Iordachita I. (2010) Development of a pneumatic robot for MRI-guided transperineal prostate biopsy and brachy therapy: New approaches. IEEE International Conference on Robotics and Automation 2010, pp. 2580-2585.
Sridhar AN, Hughes-Hallett A, Mayer EK, Pratt PJ, Edwards PJ, Yang G-Z, Darzi AW and Vale JA. (2013) Image-guided robotic interventions for prostate cancer. Nature reviews Urology 10: pp. 452-462.
Stoianovici D, Kim C, Petrisor D, Jun C, Lim S, Ball MW, Ross A, Macura KJ and Allaf ME. (2017) MR safe robot, FDA clearance, safety and feasibility of prostate biopsy clinical trial. IEEE/ASME Transactions on Mechatronics 22: pp. 115-126.
Stoianovici D, Patriciu A, Petrisor D, Mazilu D and Kavoussi L. (2007) A new type of motor: pneumatic step motor. IEEE/ASME Transactions on Mechatronics 12: 98-106.
Thorley DA. (2004) Fluid transients in pipeline systems: ASME Press.
Tzifa A, Krombach GA, Kramer N, Kruger S, Schiitte A, von Walter M, Schaeffter T, Qureshi S, Krasemann T and Rosenthal E. (2010) Magnetic Resonance-Guided Cardiac Interventions Using Magnetic Resonance-Compatible Devices. Circulation: Cardiovascular Interventions 3: pp. 585-592.
Wang W, Dumoulin CL, Viswanathan AN, Tse ZT, Mehrtash A, Loew W, Norton I, Tokuda J, Seethamraju RT and Kapur T. (2015) Real-time active MR-tracking of metallic stylets in MR-guided radiation therapy. Magnetic resonance in medicine 73: pp. 1803-1811.
Wang X, Fu DKC, Dong Z, Lee K-H, Wang K, Fang G, Lee S-L, Lee APW and Kwok K-W. (2018) Experimental Validation of Robot-assisted Cardiovascular Catheterization: Model-based versus Model-free Control, International Journal of Computer Assisted Radiology and Surgery, 8 pages.
Whitney JP, Chen T, Mars J and Hodgins JK. (2016) A hybrid hydrostatic transmission and human-safe haptic telepresence robot, IEEE International Conference on Robotics and Automation, pp. 690-695.
International Search Report and Written Opinion in corresponding PCT Application No. PCT/IB2019/051877, mailed Jun. 27, 2019.

\* cited by examiner

FLUID POWERED MASTER-SLAVE ACTUATION FOR MRI-GUIDED INTERVENTIONS

CROSS-REFERENCE TO RELATED APPLICATIONS

The present application is a U.S. National Phase Application under 35 U.S.C. § 371 of International Patent Application No. PCT/IB2019/051877, filed Mar. 8, 2019 which claims priority from the U.S. Provisional Patent Application Ser. No. 62/640,302 filed Mar. 8, 2018, both of which are incorporated herein by reference in their entirety. The present application is also a continuation-in-part of U.S. Non-Provisional application Ser. No. 15/630,406 filed Jun. 22, 2017 (now U.S. Pat. No. 11,490,975 issued Nov. 8, 2022), which claims priority to U.S. Provisional Application Ser. No. 62/354,211 filed Jun. 24, 2016, both of which are also incorporated herein by reference in their entireties.

FIELD OF INVENTION

The present invention relates to the actuation of medical robots, and particularly surgical robots for magnetic resonance imaging (MRI)-guided interventions.

BACKGROUND

The following references are incorporated herein by reference in their entirety:

[1] ASTM. (2006) Designation: F2119-07, Standard Test Method for Evaluation of MR Image Artifacts from Passive Implants, West Conshohocken, PA: American Society for Testing and Materials (ASTM) International

[2] ASTM. (2013) Designation: F2503-13, Standard Practice for Marking Medical Devices and Other Items for Safety in the Magnetic Resonance Environment, West Conshohocken, PA: American Society for Testing and Materials (ASTM) International

[3] Blanco Sequeiros R, Ojala R, Kariniemi J, Perälä J, Niinimäki J, Reinikainen H and Tervonen O. (2005) MR-guided interventional procedures: a review. Acta Radiologica 46: 576-586.

[4] Burkhard N, Frishman S, Gruebele A, Whitney J P, Goldman R, Daniel B and Cutkosky M. (2017) A rolling-diaphragm hydrostatic transmission for remote MR-guided needle insertion. IEEE International Conference on Robotics and Automation 2017 1148-1153.

[5] Chen Y, Kwok K-W, Ge J, Hu Y, Fok M, Nilsson K R and Tse Z T H. (2014a) Augmented reality for improving catheterization in magnetic resonance imaging-guided cardiac electrophysiology therapy. Journal of Medical Devices 8: 020917.

[6] Chen Y, Kwok K-W and Tse Z T H. (2014b) An MR-conditional high-torque pneumatic stepper motor for MRI-guided and robot-assisted intervention. Annals of biomedical engineering 42: 1823-1833.

[7] Cheung C L, Lee K-H, Guo Z, Dong Z, Leong M C W, Lee A P W, Kwok K-W and Chen Y. (2016) Kinematic-model-free positional control for robot-assisted cardiac catheterization. Proceedings of The Hamlyn Symposium on Medical Robotics. The Conference Proceeding is available at http://hamlyn.doc.ic.ac.uk/hsmr/programme/symposium-proceedings.

[8] Chinzei K, Hata N, Jolesz F A and Kikinis R. (2000) MR compatible surgical assist robot: System integration and preliminary feasibility study. MICCAL 921-933.

[9] Comber D B, Pitt E B, Gilbert H B, Powelson M W, Matijevich E, Neimat J S, Webster III R J and Barth E J. (2016a) Optimization of curvilinear needle trajectories for transforamenal hippocampotomy. Operative Neurosurgery 13: 15-22.

[10] Comber D B, Slightam J E, Gervasi V R, Neimat J S and Barth E J. (2016b) Design, additive manufacture, and control of a pneumatic mr-compatible needle driver. IEEE Transactions on Robotics 32: 138-149.

[11] Feng Y, Guo Z, Dong Z, Zhou X-Y, Kwok K-W, Ernst S and Lee S-L. (2017) An efficient cardiac mapping strategy for radiofrequency catheter ablation with active learning. International Journal of Computer Assisted Radiology and Surgery: 1-9.

[12] Fox R W, McDonald A T and Pritchard P J. (1998) Introduction to fluid mechanics, New York: John Wiley & Sons

[13] Fritz J, Thomas C, Clasen S, Claussen C D, Lewin J S and Pereira P L. (2009) Freehand real-time MRI-guided lumbar spinal injection procedures at 1.5 T: feasibility, accuracy, and safety. American Journal of Roentgenology 192: W161-W167.

[14] Ganesh G, Gassert R, Burdet E and Bleuler H. (2004) Dynamics and control of an MRI compatible master-slave system with hydrostatic transmission. IEEE International Conference on Robotics and Automation 2004 1288-1294.

[15] Groenhuis V, Siepel F J, Veltman J and Stramigioli S. (2017a) Design and characterization of Stormram 4: an MRI-compatible robotic system for breast biopsy. IEEE/RSJ International Conference on Intelligent Robots and Systems.

[16] Groenhuis V, Veltman J, Siepel F J and Stramigioli S. (2017b) Stormram 3. IEEE Robotics & Automation Magazine 1070.

[17] Guo Z, Dong Z, Lee K-H, Cheung C L, Fu H-C, Ho J D L, He H, Poon W-S, Chan D T M and Kwok K-W. (2018) Compact Design of a Hydraulic Driving Robot for Intra-operative MRI-guided Bilateral Stereotactic Neurosurgery IEEE Robotics and Automation Letters (Accepted).

[18] Guo Z, Lun T T L, Chen Y, Su H, Chan D T M and Kwok K-W. (2016) Novel design of an MR-safe pneumatic stepper motor for MRI-guided robotic interventions. Proceedings of The Hamlyn Symposium on Medical Robotics. The Conference Proceeding is available at http://hamlyn.doc.ic.ac.uk/hsmr/programme/symposium-proceedings.

[19] Helbich T, Rudas M, Haitel A, Kohlberger P, Thurnher M, Gnant M, Wunderbaldinger P, Wolf G and Mostbeck G. (1998) Evaluation of needle size for breast biopsy: comparison of 14-, 16-, and 18-gauge biopsy needles. AJR. American journal of roentgenology 171: 59-63.

[20] Kahn T and Busse H. (2012) Interventional magnetic resonance imaging: Springer.

[21] Kinoshita M, McDannold N, Jolesz F A and Hynynen K. (2006) Targeted delivery of antibodies through the blood-brain barrier by MRI-guided focused ultrasound. Biochemical and biophysical research communications 340: 1085-1090.

[22] Kwok K-W, Chow G C, Chau T C, Chen Y, Zhang S H, Luk W, Schmidt E J and Zion T T. (2014a) FPGA-based acceleration of MRI registration: an enabling technique for improving MRI-guided cardiac therapy. Journal of Cardiovascular Magnetic Resonance 16: W11.

[23] Kwok K-W, Lee K-H, Chen Y, Wang W, Hu Y, Chow G, Zhang S, Stevenson W, Kwong R and Luk W. (2014b)

Interfacing Fast Multi-phase Cardiac Image Registration with MRI-based Catheter Tracking for MRI-guided Electrophysiological Ablative Procedures. Circulation 130: A18568.

[24] LaRiviere M J and Gross R E. (2016) Stereotactic Laser Ablation for Medically Intractable Epilepsy: The Next Generation of Minimally Invasive Epilepsy Surgery. Frontiers in surgery 3.

[25] Lee K-H, Fu D K C, Guo Z, Dong Z, Leong M C W, Cheung C-L, Lee A P W, Luk W and Kwok K-W. (2018) MR Safe Robotic Manipulator for MRI-guided Intracardiac Catheterization. IEEE/ASME Transactions on Mechatronics (Accepted).

[26] Mortensen J, Talbot S and Burkart J A. (1990) Cross-sectional internal diameters of human cervical and femoral blood vessels: Relationship to subject's sex, age, body size. The Anatomical Record 226: 115-124.

[27] Pondman K M, Fiitterer J J, ten Haken B, Kool L J S, Witjes J A, Hambrock T, Macura K J and Barentsz J O. (2008) MR-guided biopsy of the prostate: an overview of techniques and a systematic review. European urology 54: 517-527.

[28] Prince M, Novelline R, Athanasoulis C and Simon M. (1983) The diameter of the inferior vena cava and its implications for the use of vena caval filters. Radiology 149: 687-689.

[29] Rafii-Tari H, Payne C J and Yang G-Z. (2014) Current and emerging robot-assisted endovascular catheterization technologies: a review. Annals of biomedical engineering 42: 697-715.

[30] Rahmathulla G, Recinos P F, Kamian K, Mohammadi A M, Ahluwalia M S and Barnett G H. (2014) MRI-guided laser interstitial thermal therapy in neuro-oncology: a review of its current clinical applications. Oncology 87: 67-82.

[31] Song S-E, Cho N B, Fischer G, Hata N, Tempany C, Fichtinger G and Iordachita I. (2010) Development of a pneumatic robot for MRI-guided transperineal prostate biopsy and brachytherapy: New approaches. IEEE International Conference on Robotics and Automation 2010 2580-2585.

[32] Sridhar A N, Hughes-Hallett A, Mayer E K, Pratt P J, Edwards P J, Yang G-Z, Darzi A W and Vale J A. (2013) Image-guided robotic interventions for prostate cancer. Nature reviews Urology 10: 452-462.

[33] Stoianovici D, Kim C, Petrisor D, Jun C, Lim S, Ball M W, Ross A, Macura K J and Allaf M E. (2017) MR safe robot, FDA clearance, safety and feasibility of prostate biopsy clinical trial. IEEE/ASME Transactions on Mechatronics 22: 115-126.

[34] Stoianovici D, Patriciu A, Petrisor D, Mazilu D and Kavoussi L. (2007) A new type of motor: pneumatic step motor. IEEE/ASME Transactions on Mechatronics 12: 98-106.

[35] Thorley D A. (2004) Fluid transients in pipeline systems: ASME Press.

[36] Tzifa A, Krombach Gb A, Kramer N, Krüger S, Schutte A, von Walter M, Schaeffter T, Qureshi S, Krasemann T and Rosenthal E. (2010) Magnetic Resonance-Guided Cardiac Interventions Using Magnetic Resonance-Compatible Devices. Circulation: Cardiovascular Interventions 3: 585-592.

[37] Wang W, Dumoulin C L, Viswanathan A N, Tse Z T, Mehrtash A, Loew W, Norton I, Tokuda J, Seethamraju R T and Kapur T. (2015) Real-time active MR-tracking of metallic stylets in MR-guided radiation therapy. Magnetic resonance in medicine 73: 1803-1811.

[38] Wang X, Fu D K C, Dong Z, Lee K-H, Wang K, Fang G, Lee S-L, Lee A P W and Kwok K-W. (2018) Experimental Validation of Robot-assisted Cardiovascular Catheterization: Model-based versus Model-free Control. International Conference on Information Processing in Computer-Assisted Interventions 2018. (Accepted).

[39] Whitney J P, Chen T, Mars J and Hodgins J K. (2016) A hybrid hydrostatic transmission and human-safe haptic telepresence robot. IEEE International Conference on Robotics and Automation 2016 690-695.

MRI superiority is well known over other imaging modalities, providing non-invasive and non-ionizing radiation, high-contrast imaging in particular for soft tissues, and also being capable of monitoring temperature changes during thermal therapy procedures, subtle morphological and pathological changes. These advantages have prompted MRI for the vibrant adoption in surgical interventions, ranging from neurosurgery, cardiac ablation, prostate biopsies to breast biopsies. However, MRI-compatible mechatronics is still challenged, in particular to maintain zero interference of its operation during the imaging.

The standard to quantify an MRI device safety was defined by the U.S. Food and Drug Administration (FDA), which followed the device's classification (ASTM F2503) by the American Society for Testing and Materials (ASTM) as "MR Safe", "MR Conditional" and "MR Unsafe". Physically, the electromagnetic (EM) field inside MRI scanner consists of 1) a homogeneous static field, 2) a pulsed gradient magnetic field, and 3) a pulsed radio frequency (RF) field. A device is considered MR safe if it poses no known hazards in any MRI environments.

SUMMARY OF THE INVENTION

The present invention provides a pair of cylinders connected via a long tube, which is sealed by a rolling diaphragm at the slave side and/or master side to produce low-friction transmission. Methods to integrate these components to generate bidirectional continuous rotation are also provided. These methods address challenges for MRI actuations including limited stroke and unidirectional actuation of a rolling diaphragm.

In the first aspect, an integrated fluid-powered (e.g. pneumatic, hydraulic) transmission system for MRI-guided interventions which can achieve infinite and continuous rotary motion with positional and torque control in an MR environment without interference by the magnetic resonance is provided. The system comprises at least a control unit (or interchangeably referred to "master unit") with a plurality of cylinders where each of the cylinders is inserted on the bottom side with a piston and partially encloses the piston in the presence of a seal positioned within the cylinder between the piston and the top side of the cylinder; a slave unit with a plurality of cylinders where each of the cylinders is inserted on the bottom side with a piston and partially encloses the piston in the presence of a seal positioned within the cylinder between the piston and the top side of the cylinder; and a plurality of tubes where each of the tubes connects one master unit cylinder to a respective slave unit cylinder by inserting one end of the tube into an opening of the top side of the master unit cylinder and the other end of the tube into an opening of the top side of the slave unit cylinder in order to form a pair of master/slave cylinder pair, wherein each piston is spaced apart from a lateral surface of its respective cylinder. The tubes are preferably filled with pressurized fluid and said pressurized fluid is retained inside the tubes. To ensure an efficient transmission of pressure from the pressurized fluid to the piston head, a rolling diaphragm configured to seal the pressurized fluid inside the tubes is designed to have a shape matching the shape of the piston head and the cylinder interior wall such that a gap between the piston head and the cylinder interior wall can only accommodate a single folding of the rolling diaphragm. One or more piston rods of either or both of the master and slave units are configured to pass through a centre of an output axis of the rotary motion with a corresponding fixed joint at a periphery of a rotating plate situated at the centre of the output axis of the rotary motion such that output force from each of the corresponding piston rods does not transmit to the centre of the output axis of the rotary motion directly but acts on the rotation plate first before being transmitted to the centre of the output axis of the rotary motion in order to avoid singularity.

In one embodiment, the master unit is disposed in a control room while the slave unit is disposed in an MRI operating room. The master unit and slave unit are connected through a plurality of fluid-filled tubes which run through the penetration panel that contains RF-filters and waveguides and sits between the MRI operating room and the control room.

The actuation unit can comprise three or more piston-based cylinders. The cylinders can provide action-and-reaction transmission through a long hydraulic tube (about 10 meters) that passes through a waveguide in between the MRI and control room. By integrating three or more pairs of piston-based cylinders at a slave side, an actuation unit can be constructed. Different configurations are available for the cylinders' arrangements, e.g. parallel, axial, or radial. The displacement of each cylinder rod can be precisely adjusted by a remote-control method through hydraulic pipelines. Based on the kinematic and dynamic models of the integrated transmission, the positional or torque outputs can be controlled by adjusting the combination of output positions or torques of the cylinders.

The components of an actuation unit are made of MR-safe/compatible materials and the fluid can be transmitted via semi-rigid (for example, nylon) tubes. As it is also actuated by hydraulic/pneumatic power, the whole unit is MR-safe and minimizes imaging interference in an MR environment. Embodiments of the present invention provide an MR-safe actuation in all MRI-guided (robot-assisted) procedures, e.g. electrophysiology (EP) catheterization for heart rhythm disorders, stereotactic neurosurgery for movement disorders, and prostate biopsy. Serving as a basic unit, usually more than one actuator can be implemented in an autonomous device/robot. The actuators are low cost and can be designed for single-use and consumable for easy sterilization.

DETAILED DESCRIPTION

Embodiments of the present invention provide an MR-safe integrated fluid-powered transmission method and system, which is designed for the actuation of medical equipment or robots in an MR environment. The transmission method can provide continuous bilateral or bidirectional actuation with unlimited range via long hydraulic tubes (e.g., 10 m), with controllable output position and torque. Embodiments of the present invention can be installed in various MRI-guided robotic platforms for actuation, such as endovascular procedures, neurosurgery, prostate surgery, or breast biopsy.

Figure 1:
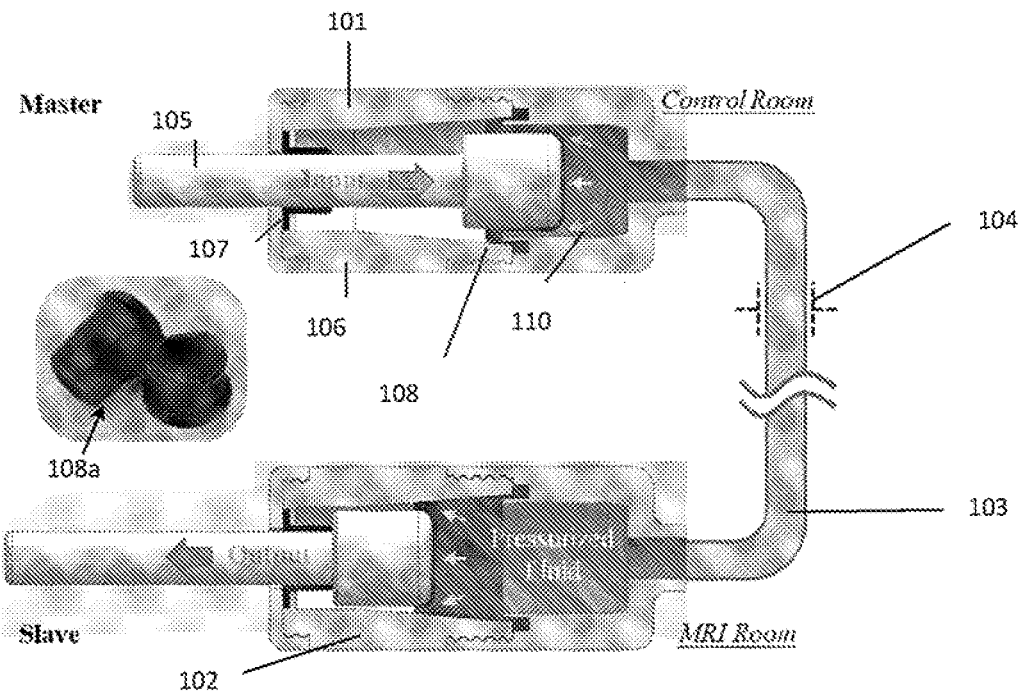
FIG. 1 shows a diagram illustrating a pair of cylinders enabling MR-safe power transmission through a long hydraulic tube via a waveguide in between a control room (master control side) and an MRI suite (slave robot side).

The basic components of the integrated fluid transmission system are a pair of piston-based cylinders (101, 102) being situated in a control room and an MRI room, respectively, as seen in FIG. 1, which enable action-and-reaction transmission via a long fluid tube 103 that passes through a wave guide 104 in between the MRI room and the control room.

Fluid can be filled in the pipelines of the long fluid tube 103 to transmit power in both directions toward the pair of piston-based cylinders (101, 102). The components, including piston rods 105, cylindrical housing 106, and bushings 107, are made of MR-safe or MR-conditional material(s). The cylinders (101, 102) contain rolling diaphragms 108 and/or other types of seals (e.g. sliding contact seals) to provide fluid sealing. For the actuators using sealed rolling diaphragms 108$a$, the static contact and sliding friction between the seal and cylinder can be inhibited. The rolling diaphragms 108 can seal a cylinder chamber 110 to retain pressurized fluid within the long fluid tube 103. To ensure symmetric rolling and constraining undesired ballooning/stretching of the diaphragm, the shapes of the piston head and cylinder wall are designed to tightly fit with the diaphragm hat, so that the gap in between can only accommodate a single folding of the diaphragm itself. As a result, the pressure reaction of the rolling diaphragm can be efficiently transmitted to the piston head.

By integrating three or more pairs of piston-based cylinders, an actuation unit can be constructed. Different configurations are available for the cylinders' arrangements, e.g. parallel, axial, or radial. The exemplary design is a radial configuration with 3 pairs of cylinders.

Figure 2:
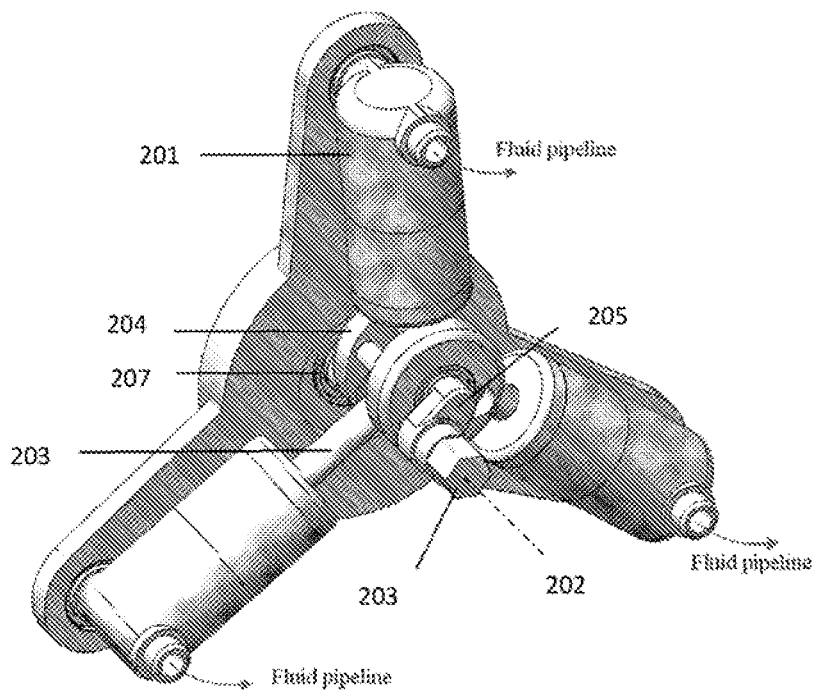
FIG. 2 shows a diagram illustrating an MR-safe continuous actuator slave unit with three radially-placed cylinders.

In an embodiment of the present invention, the integrated actuation unit comprises three or more cylinders with various arrangement methods. The actuation unit can provide an infinite range of bidirectional continuous rotation. FIG. 2 shows a model drawing of an actuator design having three cylinders, in which each cylinder 201 is radially placed/moved about the central output axis 202 at a 120° interval. The piston rods of the three cylinders can be coupled with an output shaft 203 via a rotating plate 204 and a crankshaft 205. The rotating plate 204 can be inserted into a bearing 207 to constrain the rotating plate to rotational movement. The three-cylinder design can avoid singularity, in which the input force from the cylinders cannot be transmitted as output torque. This can occur in similar crank-shaft mechanisms with one or two cylinder(s), in which all the piston rods pass through the center of the output axis 202. This mechanism can reduce motion control, particularly when the actuator is rotating at low speed without sufficient momentum to move beyond such a singularity position. A three-cylinder configuration of the present invention, therefore, can become the primitive design to provide controllable and bi-directional rotary motion.

Figure 3:
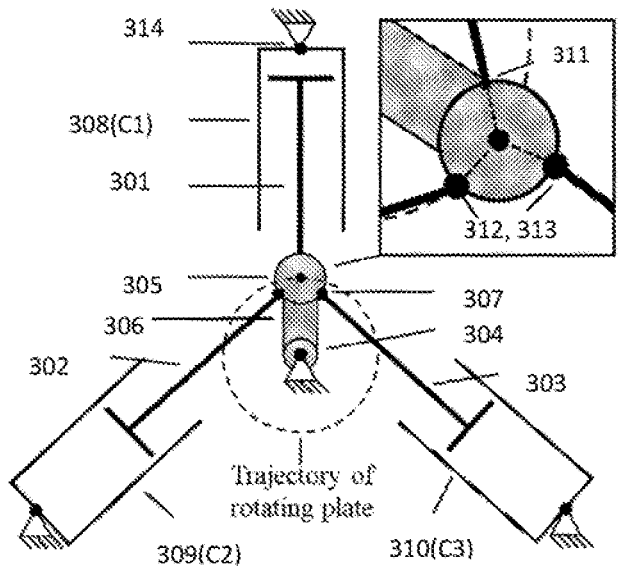
FIG. 3 shows a schematic diagram of an MR-safe continuous actuator slave unit with three radially-placed cylinders.

Three piston rods 301, 302, and 303 can be coupled with the output shaft 304 via a rotating plate 305 and a crankshaft 306, as shown in FIG. 3. Rather than directly attaching all the rods to the crankshaft 306, the rotating plate 305 connects to a piston shaft joint 307 of each of the rods 301, 302, and 303 within the limited space and allows the cylinders 308(C1), 309(C2), and 310(C3) to be arranged in the same plane. However, if the directions of output forces from the rods 301, 302, and 303 deviate from the center of the plate 305, this mechanical arrangement can introduce an uncontrolled twist of the rotating plate 305. To inhibit the twist, the rod 301 of cylinder 1 308(C1) is fixed with the plate 305 with a fixed joint 311 and the rods 302, 303 of the other two cylinders 309(C2), 310(C3) can revolve around the revolving joints 312, 313. During actuation, each cylinder 308(C1), 309(C2), and 310(C3) can sway about the cylinder anchoring joint 314 to keep the axis coincident with the axis of the rod. This can minimize the lateral force between the piston rod and bushing, as well as inhibit the possibility that the diaphragm collides with the cylinder chamber wall. In this way, the friction between the rod and bushing can be reduced, enhancing the durability of the diaphragm as well.

More than three cylinders can be configured in the actuation unit and thereby increasing the output torque of the actuation unit. With the exception of being placed radially against the crank/eccentric shaft, the cylinders can also be arranged axially or in parallel, as shown in FIGS. 6 and 7.

Figure 5:
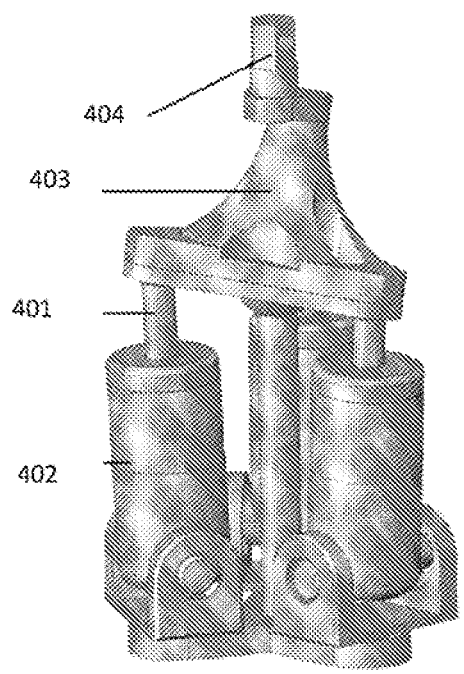
FIG. 5 shows a diagram illustrating an MR-safe continuous actuator slave unit with three axially placed cylinders.

An MR-safe continuous actuator unit can be configured to have three axially placed cylinders, as seen in FIG. 5. Each piston rod 401 of each slave unit cylinder 402 is attached axially to an eccentric shaft 403. The eccentric shaft is connected to an output shaft 404. The slave unit cylinders can be evenly spaced apart from each other around the eccentric shaft 403.

Figure 6:
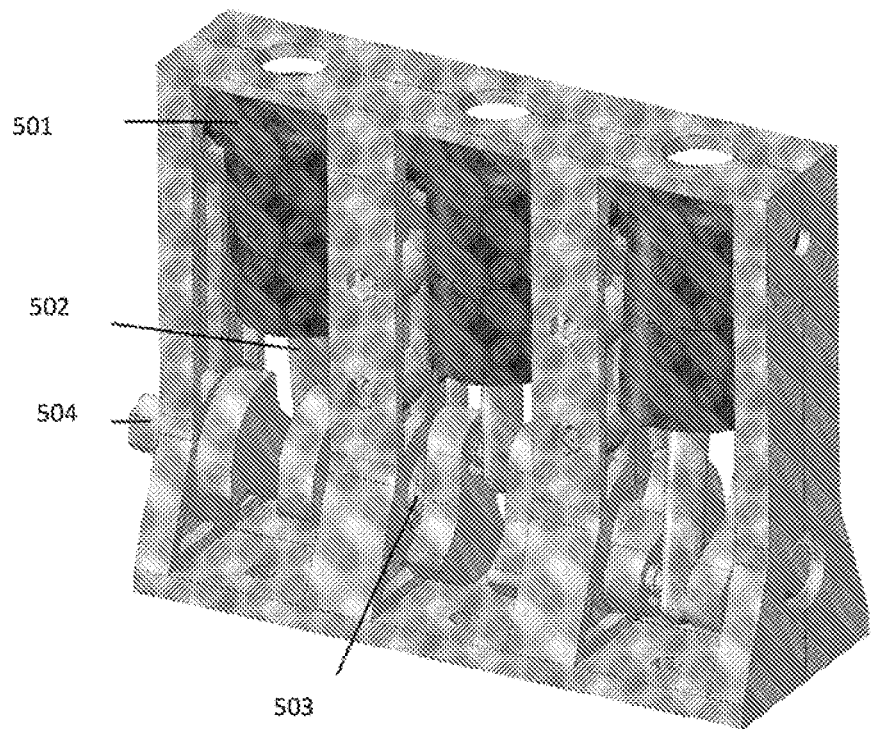
FIG. 6 shows a diagram illustrating an MR-safe continuous actuator slave unit with three cylinders placed in parallel.
Figure 7:
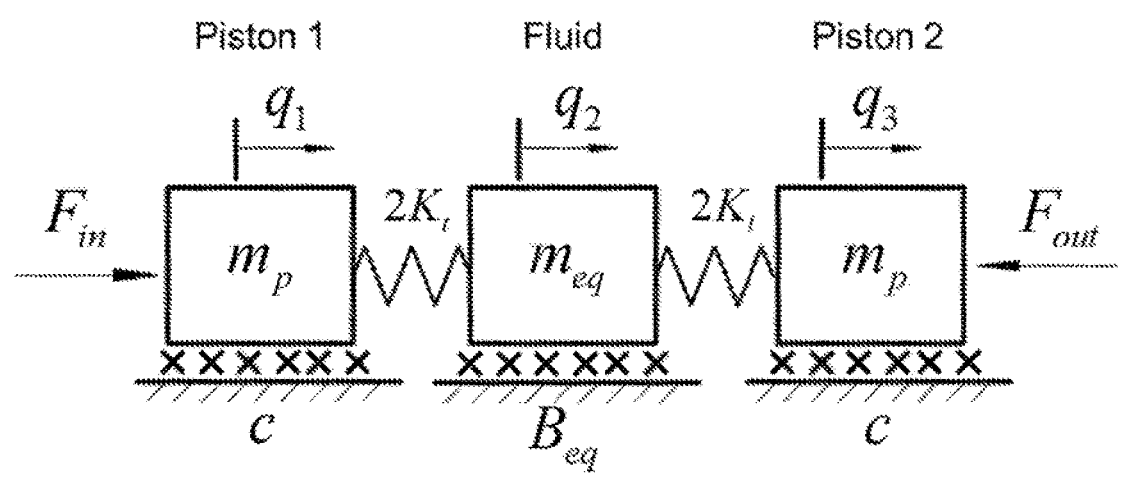
FIG. 7 is a diagram of the dynamics parameters of a single transmission pipeline.

An MR-safe continuous actuator unit can be configured to have three cylinders placed in parallel, as seen in FIG. 6. Each unit cylinder 501 is positioned in parallel with the other unit cylinders and contained within a housing unit. Each piston 502 is connected to a crank shaft 503, and the crank shaft 503 is connected to an output shaft 504.

The actuation unit can be made of MR-safe/conditional materials (e.g. plastics/polymers) and the power transmission can rely on fluid (hydraulics/pneumatics) inside of semi-rigid (e.g. nylon) tubes. Thus, the whole unit is MR-safe and minimizes imaging interference in an MR environment.

In an embodiment of the present invention, a master-slave system is adopted, in which the master unit can actuate a passive slave unit via two long hydraulic/pneumatic lines. The slave unit can be placed in the MRI room and is an actuation unit with three or more cylinders; the master part can be placed in the control room and comprises cylinders driven by DC motor(s). These master side cylinders can be incorporated into a similar structure as a slave unit, or separately controlled. By tuning the cross-sectional areas of the master and slave cylinders, a certain transmission ratio can be naturally formed without employing an additional gearbox.

To enhance transmission efficiency, the pair of pipelines can be pre-loaded with fluid at the same fluid pressure (>0.05 MPa). This increases the transmission stiffness by two means: 1) compressing any micro air bubbles that were inadvertently drawn into the pipelines during their connection; and 2) pre-stretching the seals (e.g. rolling diaphragms) that are naturally flexible in shape.

The transmission method can achieve positional and torque control in an MRI environment. The feed-forward continuous positional control can be realized by adjusting the combination of output positions of the pistons. By integrating rolling-diaphragm-sealed cylinders, the displacement of each cylinder rod can be precisely adjusted by a remote-control method through hydraulic pipelines that can be more than 10 meters. Then according to the kinematics, relations of the displacements can be found in order to generate a specific output angle with continuous motion. To achieve torque control and obtain more accurate positional control, MR-safe/conditional sensors can be integrated to provide feedback. Based on the feedback data and the kinematic/dynamic model of the fluid transmission, various functions can be achieved, including steady or controllable output velocity/torque and backlash compensation.

The kinematic model of the three-cylinder actuation unit can be derived as the following.

Figure 4:
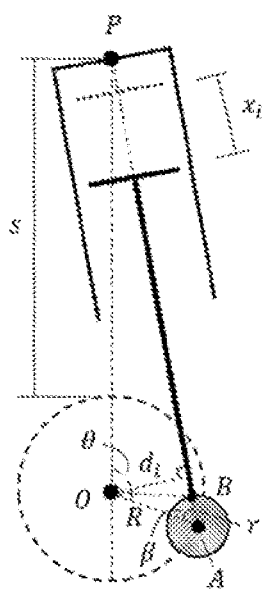
FIG. 4 shows a schematic diagram of one cylinder within the actuator slave unit with three radially-placed cylinders.

Key kinematics parameters of a single cylinder in FIG. 4 are depicted in Table 1. All the components, except for the seal, are considered as rigid bodies. Unique solutions of each piston displacement, $x_i$, are obtainable, corresponding to an angular position $\theta$ of the output shaft. By applying Cosine Law for the triangle $\triangle OAP$ in FIG. 4, the piston displacement of the cylinder C1 can be calculated as:

$$x_i(\theta) = \sqrt{(s+R)^2 R^2 - 2R(s+R)\cos\theta} - s \qquad (1)$$

where R is the radius of the crankshaft and s is the distance from point P to the nearest point on crankshaft trajectory. As the three pistons are evenly placed in a circle, cylinder C2 and C3 have phase differences of $2\pi/3$ and $4\pi/3$ with cylinder C1. Therefore, the piston displacements of cylinder C2 and C3, the displacements, $x_2$ and $x_3$, can be derived by re-phasing the $\theta$, respectively, with $(\theta-2\pi/3)$ and $(\theta-\pi/3)$ in equation (1). The misalignment is negligible for the installation of the rotating plate.

TABLE 1

| Parameter | Description |
|---|---|
| $x_i$ | Piston displacement |
| s | Distance from point P to the nearest point on crankshaft trajectory |
| $\theta$ | Angular position of the output shaft |
| $\beta$ | Angle between the piston rod and the direction of the rotating plate relative to the output axis |
| r | Radius of rotating plate |
| R | Radius of crankshaft |
| $d_i$ | Distance between the center line of the $i^{th}$ piston rod and the rotation axis of output shaft |

The dynamic model of the three-cylinder actuation unit is derived as follows. Each cylinder of the actuation unit can generate a unidirectional force, which comes from the positive pressure within the pipeline. Torques towards the output shaft, which are transferred from the forces of the cylinders, can then be described as $\tau_i = F_i \cdot d_i$, where $F_i$ is the force provided by the $i^{th}$ cylinder and $d_i$ is the distance between the center line of the $i^{th}$ piston rod and the rotation axis of the output shaft. $d_i$ can be calculated as $d_i = R \cdot \sin \beta_i$, where R is the rotational radius and $\beta_i$ can be further calculated by Sine Law as:

$$\sin\beta_i = \frac{s \cdot \sin(\theta - \varphi_i)}{\sqrt{s^2 + R^2 - 2s \cdot R\cos(\theta - \varphi_i)}} \qquad (2)$$

where $\theta$ is the angular position of the output shaft and $\varphi_i$ is the phase for the $i^{th}$ cylinder, with values of $2\pi/3 \cdot (i-1)$ for i=1,2,3. The torques generated by the three cylinders are summed at the crankshaft as:

$$\Sigma_{i=1}^{3} \tau_i = I_r \ddot{\theta} + \tau_0 \qquad (3)$$

where $I_r$ is the inertia of the rotational components, $\ddot{\theta}$ is the angular acceleration of the output shaft.

Therefore, the correlation between the output torque and the forces provided by the cylinders, which are governed by fluid pressure, can be described by the dynamic model of the three-cylinder configuration. Torque control is then possible to be further implemented into the actuator.

A dynamic model for the fluid transmission can also be developed, with the consideration of fluid damping, inertia, and stiffness. The force, $F_{in}$, input piston is assumed to produce movement at constant velocity, with no load at the output piston ($F_{out}=0$). Analysis of damping in the hydraulic transmission lines begins with analyzing head loss, which is governed by the Bernoulli equation for steady and incompressible flow between any two points in a pipe. In this case, pipelines loss mainly contributes to head loss. Because the pipeline loss is proportional to the length, but inversely proportional to the diameters, the head loss in the cylinders is negligible when compared with that in the pipelines. The pipeline loss can be given as:

$$h_f = \frac{\lambda L_p v_f^2}{2D_{pi}} \qquad (4)$$

where $\lambda$ is the flow coefficient, $L_p$ and $D_{pi}$ are, respectively, the length and inner diameter of pipelines, $v_f$ is the fluid velocity. For laminar pipe flow, the flow rate is given by $\lambda=64/Re$, where Re denotes the Reynolds number. By observing that $F=P \cdot A$, the equivalent damping coefficient can be obtained as:

$$B_{eq} = \frac{F_{in}}{v_{in}} = 8\pi\mu L_P \left(\frac{D_{in}}{D_{pi}}\right)^4 \qquad (5)$$

where $\mu$ is the dynamic viscosity of fluid, $v_{in}$ and $D_{in}$ are the velocity of piston and diameter of cylinder at master side, on which the force is applied.

For the fluid inertia, an equivalent mass as observed at the piston is considered, which can be determined by an energy calculation:

$$m_{eq} v_{in}^2 = m_{cyl} v_{in}^2 + m_p v_f^2 \qquad (6)$$

where $m_{eq}$ is the equivalent mass, $m_{cyl}$ is the fluid mass in cylinder, and $m_p$ is the fluid mass in the pipeline.

The transmission stiffness is determined by considering pipeline compliance at first. The following equations derive the hoop stress $\sigma_\theta$ and radial stress $\sigma_r$ at the inner pipe wall in response to an applied pressure P according to Lamé Formula:

$$\sigma_\theta = P \cdot \frac{D_{pi}^2 + D_{po}^2}{D_{po}^2 - D_{pi}^2}, \sigma_r = -P \qquad (7)$$

where $D_{po}$ is the outer diameter of the pipeline. If the pipe is assumed to be made of a linear isotropic material with a modulus of elasticity E and Poisson's ratio $v$, the hoop strain is equivalent to:

$$\varepsilon_\theta = \frac{\Delta D_{pi}}{D_{pi}} = \frac{\sigma_\theta - v\sigma_r}{E} \qquad (8)$$

If the fluid volume variation inside the cylinder of input ($A_{in} \cdot \Delta x_{in}$) is equal to the variation in the pipe ($\Delta A_p \cdot L$). Then the inner diameter variation of pipe can be determined as:

$$\Delta D_{pi} \approx \frac{D_{in}^2 \cdot \Delta x_{in}}{2D_{pi} L} \qquad (9)$$

With Equations 7-9 and the assumption that the pressure comes from the input force $F_{in} = P \cdot A_{in}$, the pipeline stiffness $K_p$ observed at the piston can be derived as:

$$K_p = \frac{\pi E D_{in}^4}{8 D_{pi}^2 L} \left[\frac{D_{pi}^2 + D_{po}^2 + v D_{po}^2 - v D_{pi}^2}{D_{po}^2 - D_{pi}^2}\right]^{-1} \qquad (10)$$

The fluid stiffness due to compression can be modeled as $K_f = E_v \cdot A^2/V$, where V is the total volume of fluid and $E_v$ the fluid bulk modulus. Equivalent transmission stiffness, $K_t$, of the hydraulic transmission line is calculated as the series of pipeline compliance and fluid stiffness:

$$K_t = \frac{K_p K_f}{K_p + K_f} \qquad (11)$$

Components of the overall dynamic model of the passive fluid transmission system are shown in FIG. 7. The dynamics of the transmission line is modeled as:

$$M\ddot{q} + Kq + C\dot{q} = F \qquad (12)$$

where $$\begin{cases} M = \text{diag}\left(m_p + \frac{I_r}{R^2}, m_{eq}, m_p + \frac{I_r}{RE^2}\right) \quad C = \text{diag}(c, B_{eq}, c) \\ K = \begin{bmatrix} 2K_t & -2K_t & 0 \\ -2K_t & 4K_t & -2K_t \\ 0 & -2K_t & 2K_t \end{bmatrix} \quad F = [\,F_{in} \;\; 0 \;\; -F_{out}\,]^T \end{cases} \qquad (13)$$

In the Equation (12), $q=[q_1 \; q_2 \; q_3]^T$ denotes the matrix containing displacements of input piston ($q_1$), fluid ($q_2$) and output piston ($q_3$). c is the damping coefficient introduced by rolling diaphragm. $F_{in}$ and $F_{out}$ are the input and output force, respectively. The state space function can be given as following:

$$\begin{bmatrix} \dot{q} \\ \ddot{q} \end{bmatrix} = \begin{bmatrix} 0 & I \\ -M^{-1}K & -M^{-1}C \end{bmatrix} \begin{bmatrix} q \\ \dot{q} \end{bmatrix} + \begin{bmatrix} 0 \\ M^{-1}F \end{bmatrix} \qquad (14)$$

The present invention includes, but is not limited to, the following exemplified embodiments.

Embodiment 1. An integrated actuation system for a magnetic resonance environment comprising:
  a master unit comprising:
    a plurality of master unit cylinders, each master unit cylinder having an opening at a bottom surface and an opening near a top surface opposite of the bottom surface of the master unit cylinder,
    a piston inserted within the bottom surface of each master unit cylinder and partially positioned within each master unit cylinder, and
    a seal positioned within each master unit cylinder between the piston and the top surface of the master unit cylinder to inhibit a fluid from passing across the seal,
    wherein each piston is spaced apart from a lateral surface of its respective master unit cylinder;
  a slave unit comprising:
    a plurality of slave unit cylinders, each slave unit cylinder having an opening at a bottom surface and an opening near a top surface opposite of the bottom surface of the slave unit cylinder,
    a piston inserted within the bottom surface of each slave unit cylinder and partially positioned within each slave unit cylinder, and
    a seal positioned within each slave unit cylinder between the piston and the top surface of the slave unit cylinder to inhibit fluid from passing across the seal,
    wherein each piston is spaced apart from a lateral surface of its respective slave unit cylinder; and
  a plurality of tubes, each tube connecting one master unit cylinder to a respective slave unit cylinder to form a master/slave cylinder pair, each end of the tube being inserted at the opening near the top surface of a respective cylinder of the master/slave cylinder pair.

Embodiment 2. The system of embodiment 1, wherein a body of the slave unit comprises non-ferromagnetic and MR-safe material.

Embodiment 3. The system of any of embodiments 1-2, wherein the master unit is disposed in a control room and the slave unit is disposed in an MRI operating room.

Embodiment 4. The system of any of embodiments 1-3, wherein the master unit or slave unit comprises three or more piston actuators.

Embodiment 5. The system of any of embodiments 1-4, wherein at least one of the seal comprises a rolling diaphragm or a sliding contact seal.

Embodiment 6. The system of any of embodiments 1-4, wherein the slave unit cylinders are configured radially, axially, or in parallel against an eccentric shaft.

Embodiment 7. The system of any of embodiments 1-4, wherein the slave unit cylinders are positioned radially, wherein each piston is attached to a rotating plate, and wherein all pistons are positioned in a single plane.

Embodiment 8. The system of any of embodiments 1-4, wherein the slave unit cylinders are attached radially or axially to an eccentric shaft, and wherein the slave unit cylinders are evenly spaced apart from each other around the eccentric shaft.

Embodiment 9. The system of any of embodiments 1-4, wherein the master unit cylinders and slave unit cylinders are positioned in parallel, wherein the pistons are connected to a crank shaft, and wherein the crank shaft is connected to an output shaft.

Embodiment 10. The system of any of embodiments 1-9, wherein the slave unit is connected with a second symmetric master unit at a master side by two or more tubes, wherein an electric motor at the master side drives the second symmetric master unit, and wherein the slave actuator replicates the motion simultaneously through hydraulic or pneumatic transmission.

Embodiment 11. The system of any of embodiments 1-10, wherein each piston in the slave unit is actuated by a corresponding piston in the master unit to form a master/slave piston pair, and wherein a plurality of electric motors are driving each master/slave piston pair, respectively.

Embodiment 12. The system of any of embodiments 1-11, wherein positional control of the slave unit is achieved through an inverse kinematic model of the integrated actuation system.

Embodiment 13. The system of any of embodiments 1-12, wherein torque control of the slave unit is achieved through a dynamic model of the integrated actuation system.

Embodiment 14. The system of any of embodiments 1-13, wherein the pipes are filled with fluid comprising liquid, gas, or a combination thereof.

Embodiment 15. The system according to any of embodiments 1-14, wherein the tubes comprise rigid or semi-rigid materials.

Embodiment 16. The system according to any of embodiments 1-15, wherein the tubes have sufficient length to extend from the master unit in an MRI control room to the slave unit in an MRI operating room.

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

It should be understood that the examples and embodiments described herein are for illustrative purposes only and that various modifications or changes in light thereof will be suggested to persons skilled in the art and are to be included within the spirit and purview of this application.

The experiment in Example 1 used a single-cylinder actuator. Experiments in examples 2, 3, and 4 used a three-cylinder actuator. In all tests, the master and slave parts of the transmission were connected by 10 meter semi-rigid nylon (PA 6) tubes, which had inner/outer diameters of ⅘ mm, respectively. Distilled water was employed as hydraulic fluid due to its availability and ease of implementation. The pre-loading levels of all fluid in all the pipelines were controlled by a pressurized air supply system, a pressure regulating valve and a fluid reservoir. The pre-pressurization was conducted before each operation to eliminate the backlash and ensure the symmetric folding/unfolding of the rolling diaphragms.

Example 1—Step Response of the Single Cylinder

Figure 8:
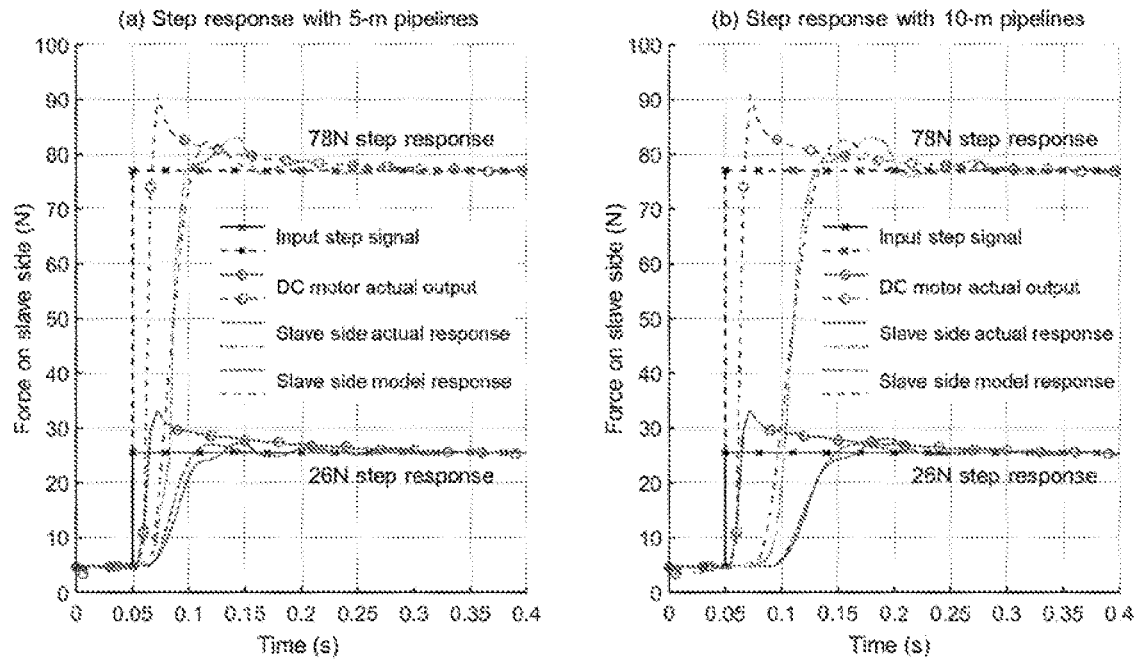
FIG. 8 is the plots of actual and model step responses with different force step inputs of single cylinder transmission with 5-m and 10-m pipelines shown in (a) and (b) respectively.

This experiment of the step response was conducted to evaluate the force transmission behavior between one pair of cylinders (see, for example, FIG. 6). At the master side, a DC motor actuated the master cylinder through a rack-and-pinion mechanism, which transmitted motor torque to linear force. The output force at the slave cylinder was measured by a force sensor fixed with a piston rod. The hydraulic fluid was preloaded at 0.05 MPa to ensure the mechanical couplings fully engaged, which corresponded to 5 N force output on slave cylinder at the initial state. Two step inputs, i.e. 26 N and 78 N, were applied on the master cylinder. The corresponding measured force response is shown in FIG. 8. Simulated results based on the dynamic model are also overlaid as green curves, predicting a similar response to the measured results. The response time is within 40 ms from the signal input and the 10% to 90% rise time is 25 ms for both step input forces even for 10-m transmission. This rise time remains constant for different input forces, depicting an important feature for a linear time-invariant system. Settling time with 5% error band is about 0.17 s. The rolling-diaphragm-sealed hydraulic transmission rapidly transmitted force, even at a 10-meter long distance. These force transmission characteristics are crucial to a highly responsive tele-operated robotic system.

Example 2—Force Transmission Performance of a Three-Cylinder Continuous Actuator The force transmission performance of the three-cylinder continuous motor was evaluated in a weight-lifting experiment. In this test, three master cylinders were independently actuated by electric motors with leadscrew drives. The output shaft was coupled to a winch of diameter Ø40 mm. The hydraulic fluid was pre-loaded at 0.1 MPa and the master-slave actuator lifted 2.5 kg at a constant velocity of 50.24 mm/s, corresponding to an output torque of 0.49 Nm and a net power of 1.23 W. The volumetric power density of the hydraulic transmission was 2.46 kW/m³. The torque/power outputs of this motor were mainly determined by the electric motor inputs at the master side. As such, the continuous motor can generate power as large as the electric motors can provide, up to the lower strength limit of the weakest component, e.g. tiny gear teeth and thin rolling diaphragms.

Example 3—Positional Frequency Response of the Three-Cylinder Continuous Actuator The dynamic performance of a three-cylinder continuous actuator was investigated with a frequency response method. No loading was added to the slave actuator. The three master cylinders were controlled using inverse kinematics. The slave actuator can thus follow the periodic sinusoidal input of the master actuator under an open-loop control, where the angular position $\theta=A \sin(\omega \cdot t)$. The amplitude was 5° and the test frequency was from 0.1 to 7 Hz. The output angular position was measured by a differential encoder coupled with the output shaft.

Figure 9:
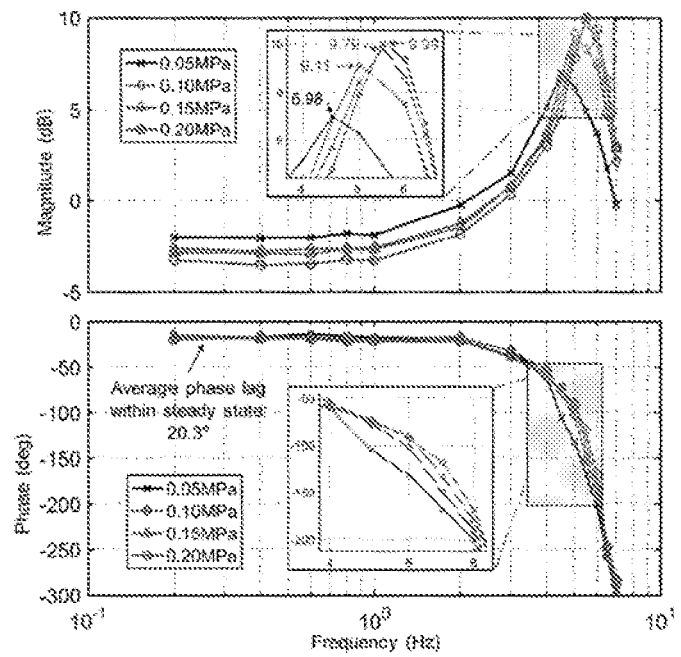
FIG. 9 is a Bode plot of a 3-cylinder actuator.

FIG. 9 illustrates the Bode plots of the "magnitude" M and the "phase-shift" $\xi$ of the continuous actuator at a steady state. Note that for a linear time-invariant system, the frequency response at a steady state becomes $\tau_{ss}=M \cdot A \sin(\omega \cdot t + \xi)$. The magnitude plot indicates that the magnification increases with the preloaded fluid pressure. The magnification value peaks at around 5 Hz, which corresponds to the natural frequency of the overall hydraulic transmission. The phase lag of the transmission is kept at around 20.3° for a low actuation frequency (<2 Hz). It was also found that increasing the preloaded fluid pressure does not significantly affect the natural frequency and phase lag. The transmission with preloaded fluid pressure 0.2 MPa had a small time delay: 60 ms and 52 ms at actuation frequencies 1 Hz and 5 Hz, respectively.

Example 4—Sinusoidal Positional Tracking of the Three-Cylinder Continuous Actuator To evaluate the accuracy of the 3-cylinder actuator with open-loop control, a positional tracking test was performed. The setup is the same as Example 3, but the periodic sinusoidal input at master side has a constant frequency of 0.05 Hz and a larger range of motion of 360°.

Figure 10:
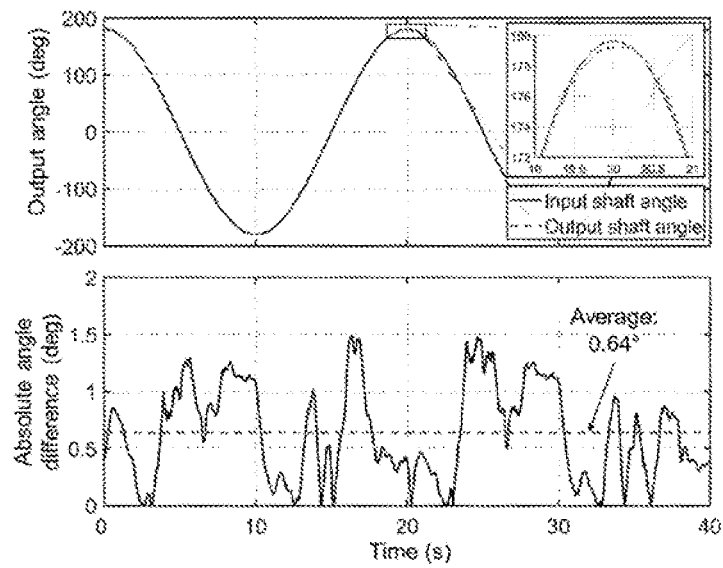
FIG. 10 is a plot of sinusoidal tracking of a 3-cylinder actuator.

The results are illustrated in FIG. 10, showing the angular position curves and the positional error. This demonstrates that the 3-cylinder continuous actuator can track the positional input over the 360° range. The average error between the input and output within one cycle is 0.64°, showing that the proposed actuator can be manipulated by open-loop control accurately.

Example 5—Robot

Figure 11:
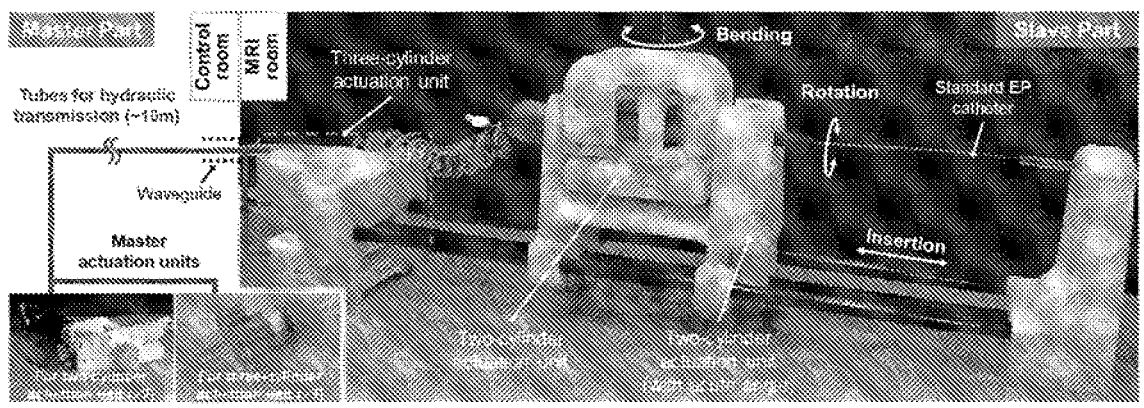
FIG. 11 is a diagram of an MR-safe catheter robot system integrating the 3-cylinder actuation unit.

Hydraulic transmissions were incorporated into a drive catheter robot capable of operating in an intraoperative MRI, as shown in FIG. 11. The robot comprised master and slave actuation in a control room and an MRI suite, respectively. To ensure MR safety and minimal interferences to the MR images, no metallic material was integrated into the slave actuation. The master units were actuated by electric motors located in the control room. A catheter holder was designed to be plugged-in with a standard EP ablation catheter (e.g., Biosense Webster Inc. or St. Jude Medical).

Figure 12:
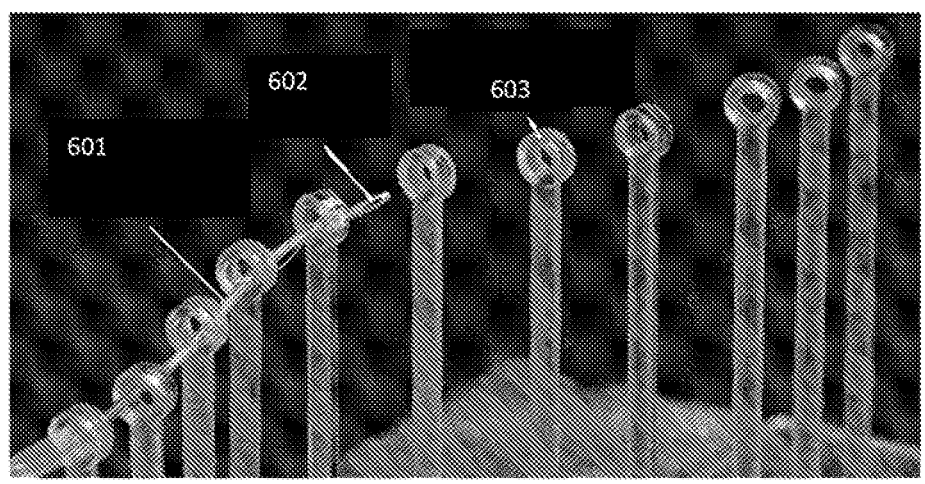
FIG. 12 shows the setup of the long-range catheter navigation for the robot.

Three hydraulic actuation units are adopted in the robot. The bending and rotation degrees of freedom (DoF) employs the two-cylinder actuation units. The rotation range is amplified by placing the two cylinders at an acute angle of 27.5°. As a result, the robot can drive with a motion range of ±45° for catheter bending and ±360° for catheter rotation. As shown in FIG. 12, an EP catheter 601 (Thermocool® Smarttouch™ Bi-directional Catheter, Biosense Webster Inc.) can be bent and steered in a full range of ±180°. A tracking device 602 can be positioned on the catheter tip in order to provide fast and accurate positional feedback. Furthermore, the three-cylinder unit is incorporated to actuate the $3^{rd}$ robot DoF. Not only does it enable the catheter advancement towards and into the human body in a range of 240 mm, but it also ensures high fidelity of pushing/pulling the catheter in short range, which is crucial for delicate EP tasks, such as electro-anatomic mapping (EAM) and radio frequency (RF) ablation.

Two sets of experiments were designed and conducted to evaluate the performance of robotic catheterization. The experiments attempt to simulate long-range navigation of a catheter, from the femoral vein to the left atrium (LA), and also emulate a short-range navigation task for pulmonary vein isolation (PVI) inside an atrial phantom model.

Figure 13:
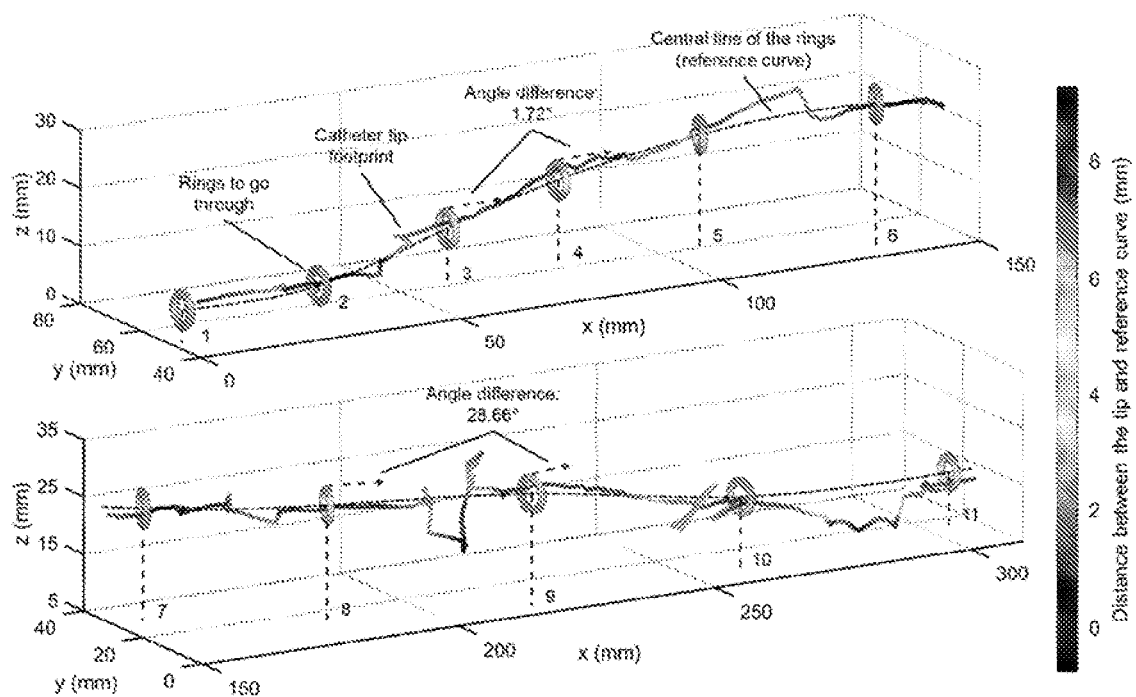
FIG. 13 is a diagram of the results showing actual footprint of the catheter tip compared with the reference curve along the series of rings of $1^{st}$-6th (upper) and 7th-11th (lower) of the long-range catheter navigation for the robot.

For a long-range catheter navigation test, eleven rings 603 (inner diameter=Ø7 mm) were placed in sequence along a 310 mm distance with an average spacing of 31 mm, as shown in FIG. 12. The detailed dimensions are shown in Table 2. A smooth curve linking the ring centers in serial simulates a path along vessel to heart chamber, as shown in FIG. 13. This task is more difficult than navigating in a human vein (inner diameter≈Ø9.4 mm) and an inferior vena cava (inner diameter≈Ø20 mm). During the task, a standard catheter 601 with an outer diameter of 8 Fr (≈Ø2.7 mm) is manipulated by the robot that is tele-controlled by a 3D motion input device (Novint Falcon, NF1-L01-004). To record the real-time position and orientation (pose) of the catheter, a 5 D-of F EM positional sensor 602 (NDI Medical Aurora) was attached near the catheter tip. An individual, who is familiar with the robot's operation, was invited to perform the task. The individual was able to look at the catheter tip to adjust the manipulation so as to pass the catheter through all eleven rings 603.

TABLE 2

| Experimental settings | | Robot performance | |
|---|---|---|---|
| No. of rings | 11 | Total time (s) | 96.0 |
| Inner diameter of the rings (mm) | 7.0 | Average time interval per ring (s) | 9.6 |
| Dimension of the setup (L × W × H mm) | 310 × 70 × 32 | Min./max. interval between two rings (s) | 1.9/19.8 |
| Avg. spacing of rings along x-axis (mm) | 31.0 | Average value of deviation (mm) | 3.03 |

The diagrams in FIG. 13 depict the catheter tip footprint along the series of 11 rings. The deviation from catheter tip to the reference curve is indicated by the color gradient. A mean value of deviation, 3.03 mm, was found throughout the entire trajectory. Most sections of navigation are smooth and closed along with the reference curve. But several sections of the tip footprint involved more deviations, particularly when the orientation difference of adjacent rings was relatively large. Dragging the catheter into the ring hole without graphic user interface (GUI)-aided navigation can be challenging.

Figure 14:
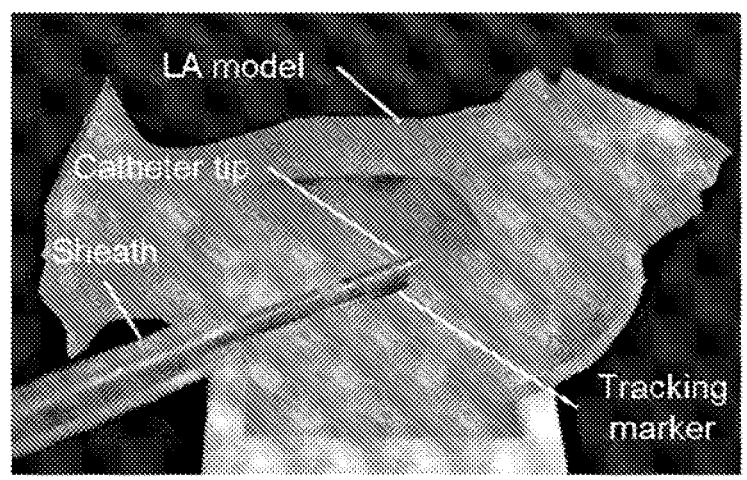
FIG. 14 shows the setup of the short-range catheter tip targeting for the robot.

For the short-range catheter tip targeting test, an LA phantom model was designed and constructed based on a patient-specific imaging data, to simulate catheter tip targeting for PVI. It was 3D-printed with soft material (Agilus-Clear, Stratasys, USA), as shown in FIG. 14. A semi-rigid sheath was fixed near the end to ensure the location of outlet was similar to the transseptal puncture through atrial septum to the LA in the PVI. The same individual, as in the last navigation task, tele-manipulated the catheter through the aid of a GUI, by which a virtual endoscopic view from the viewpoint of the catheter tip can be rendered and provided.

This endoscopic view can be constructed in an MRI environment with accurate alignment between the MR-based tracking and the imaging, both of which are measured by MRI and in the same coordinate system. The MR-tracking devices can provide fast and accurate positional feedback of the catheter tip. Meanwhile, the fast MR images can be acquired in the region around the catheter tip by means of fast image registration, to register/realign the lesions on the pre-operative EP roadmap. In this way, all the components can be interleaved virtually but with an accurate alignment under MRI.

In the lab-based experiment, the real-time position and orientation of the endoscopic view was obtained from the tracking sensor near the catheter tip. A virtual LA phantom was registered to the actual phantom before the task. Six points were predefined on the LA phantom for the registration and transformation between tracking coordinates and virtual environment. The virtual view facilitates fine placement of the catheter tip while approaching the "lesion" targets, which were prescribed on the virtual LA phantom around the pulmonary vein ostium. During the task, a "lesion" was confirmed when the catheter tip collided with the virtual LA model in the virtual view.

Figure 15:
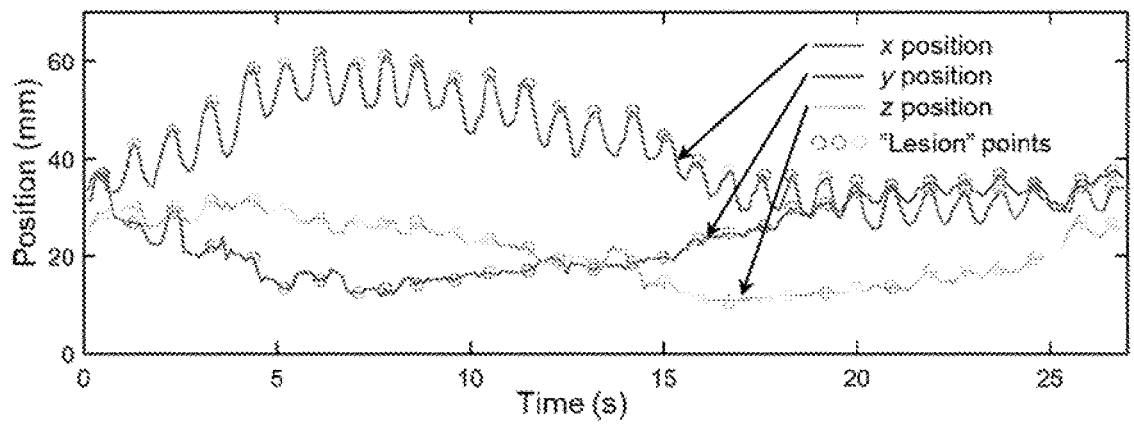
FIG. 15 is a diagram of the results showing catheter tip trajectory decouple 3 axes against time of the short-range catheter tip targeting for the robot.
Figure 16:
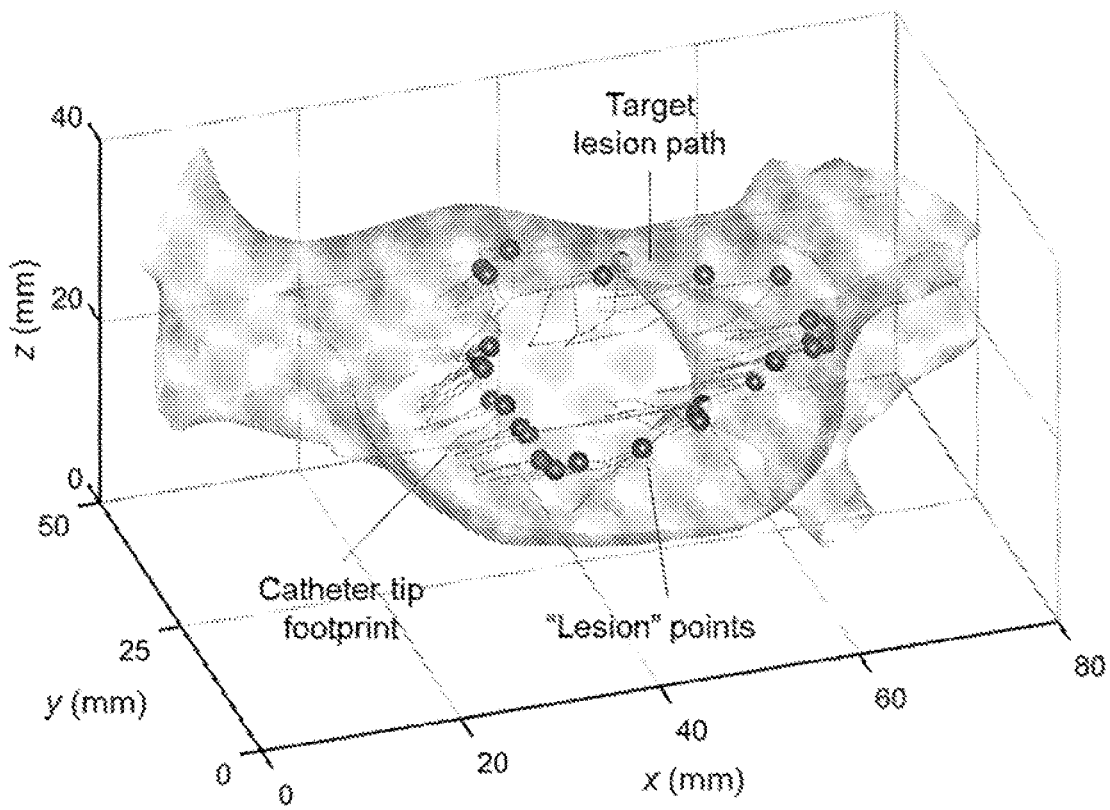
FIG. 16 is a diagram of the results showing catheter tip footprint, the 30 targeted ablation points—"lesions", and also the desired lesion targets of the short-range catheter tip targeting for the robot.

FIG. 15 illustrates the tip positions in x-, y- and z-component within 27 seconds. Since the direction of catheter insertion was close to the x-axis, reciprocating motions can be clearly observed from the curve of x position, with an average frequency of 1.1 Hz over the time range. Such fast and delicate reciprocating motions provided by the robot have potential to maintain a proper contact between catheter tip and cardiac tissue in the dynamic environment, avoiding penetration during ablation. FIG. 16 shows the front view of the results in 3D. The red dots, with a total number of 30, represent the "lesion" points, covering the complete ostium. Average/maximum deviation of these points from the "lesion" targets is 1.1/3.2 mm. The "lesions" were conducted clockwise from the view of FIG. 15. Such gradual shifting of points is also illustrated by the catheter tip footprint, which features short-range and high-fidelity.

A signal-to-noise ratio (SNR) test was conducted to evaluate the EM interference to the MR images during operation of the robot. Since the slave part of the robot shown in FIG. 11 involves exclusively non-conducting, non-metallic and non-magnetic materials, it fulfills the MR Safe classification of ASTM standard F2503-13. During the test, the slave part of the robot was operated inside a 1.5 T MRI scanner (SIGNA, General Electric Company, USA) and was placed near a commercial MRI phantom (J8931, J.M. Specialty Parts, USA) at the isocenter of the scanner. The T1-weighted fast field echo (FFE) and T2-weighted turbo spin echo (TSE) sequences were adopted to obtain the MR images.

Figure 17:
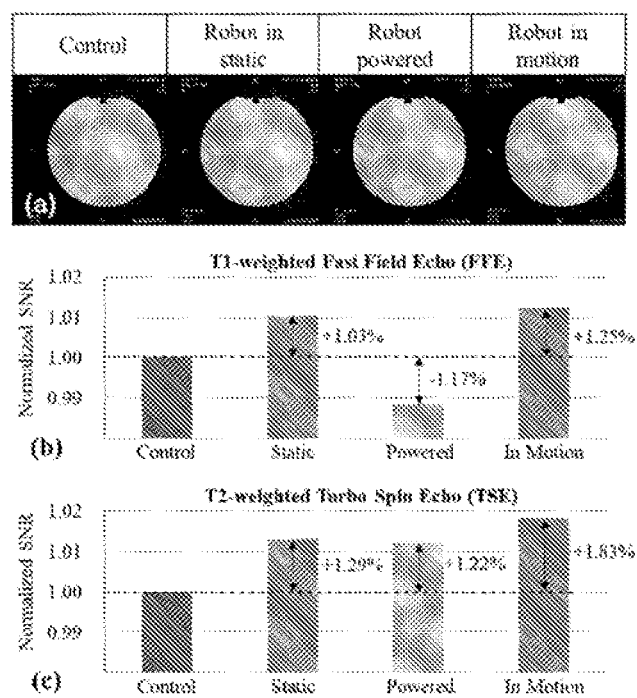
FIG. 17 is a diagram of the results showing (a) MR images of an MRI phantom placed aside the robot indicating the negligible EM interference in four different operating conditions; (b) SNR test results with the sequence of T1-weighted fast field echo; and (c) SNR test results with the sequence of T2-weighted turbo spin echo.

FIG. 17(a) shows the resultant MR images of the phantom by T2-weighted TSE under four different conditions: i) Control: only phantom placed in the scanner; ii) Static: robot involved and remained power OFF; iii) Powered: robot kept still, but with the hydraulic and electric power ON; iv) In motion: robot in operation. No observable image artifact was found in the MR images under different robot operation scenarios. The SNR analysis followed the guidelines provided by ASTM F2119-07, with the control condition served as the baseline for evaluation. FIGS. 17(b)&(c) illustrate the results of SNR analysis under the two imaging sequences.

The maximum SNR loss in the successive conditions was found within 2% only, even with the robot in full motion.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

The invention claimed is:

1. A remotely-controlled and magnetic resonance-safe actuation system for exerting continuous and bi-directional rotary motion without interference in a magnetic resonance environment, said system comprising:
at least a control unit and a slave unit being situated in different physical locations and connected by one or more pressurized fluid-filled tubes where the pressurized fluid inside the tubes is sealed by corresponding rolling diaphragms of said control and slave units such that the pressurized fluid is retained inside the tubes,
each of said control and slave units comprising at least a piston and a cylinder, a piston head of said piston and a cylinder interior wall of said cylinder of each of said control and slave units being configured in a shape to match the rolling diaphragm's shape such that a gap between said piston head and said cylinder interior wall only accommodates a single folding of the rolling diaphragm when the pressurized fluid flows towards the piston head of each of said control and slave units, and
at least one piston rod of any one or both of said control and slave units being directed toward a centre of an output axis of the rotary motion with a corresponding fixed joint at a periphery of a rotating plate situated at distance from the centre of the output axis of the rotary motion but connected thereto such that output force from each of the corresponding piston rods of said control and slave units does not transmit to the centre of the output axis of the rotary motion directly but acts on the rotation plate first before being transmitted to the centre of the output axis of the rotary motion in order to avoid singularity.

2. The system of claim 1, wherein said slave unit is made of one or more of ferromagnetic and/or magnetic resonance-safe materials.

3. The system of claim 1, wherein said control unit and said slave unit are located in a control room and an MRI operating room, respectively.

4. The system of claim 1, wherein any one or both of said control and slave units comprises at least three pairs of corresponding piston and cylinder.

5. The system of claim 1, wherein said cylinders of the slave unit are arranged radially, axially or in parallel against an eccentric shaft.

6. The system of claim 5, wherein said cylinders of the slave unit are arranged radially, the piston rod of one of the radially-arranged cylinders of the slave unit is directed toward the centre of the output axis of the rotary motion and has a fixed joint at the periphery of the rotating plate situated at a distance from the centre of the output axis of the rotary motion but is connected thereto by a crank shaft such that output force from each of the corresponding piston rods does not transmit to the centre of the output axis of the rotary motion directly but act on the rotation plate first before being transmitted to the centre of the output axis of the rotary motion in order to avoid singularity.

7. The system of claim 5, wherein each cylinder of the radially-arranged cylinders of the slave unit is placed at approximately 120° from an adjacent cylinder about the centre of the output axis of the rotary motion.

8. The system of claim 6, wherein two other piston rods of the three radially-arranged cylinders of the slave unit are fixed with two corresponding revolving joints at the periphery of the rotating plate and each of the cylinders is configured to anchor with a cylinder anchoring joint to sway about in order to keep the axis thereof consistent with the axis of the two other piston rods during actuation.

9. The system of claim 1, wherein said slave unit is connected with a second symmetric control unit by two or more of the pressurized fluid-filled tubes, and wherein an electric motor drives the second symmetric control unit, and wherein the slave unit replicates the motion simultaneously through direct hydraulic or pneumatic transmission of force from the second symmetric control unit via the pressurized fluid.

10. The system of claim 1, wherein corresponding pistons of said control and slave units are driven by a plurality of electric motors.

11. The system of claim 1, wherein said slave unit is positioned through an inverse kinematic model while output torque thereof is modulated by a dynamic model of said system.

12. The system of claim 1, wherein said pressurized fluid-filled tubes are filled with pressurized fluid of equal to or more than 0.05 MPa and one or more materials comprising gas.

13. The system of claim 1, wherein said pressurized fluid-filled tubes are made of one or more materials comprising rigid and semi-rigid materials such as nylon.

14. The system of claim 1, wherein said control and slave units are located at a distance of at least 10 meters apart from each other and are connected by fluid-filled tubes which run through the penetration panel sitting between the MRI operating room and the control room.

15. The system of claim 14, wherein said slave unit has a response time within 40 milliseconds from the time when a two-step input force is exerted on the control unit connected thereto.

16. The system of claim 15, wherein said slave unit has a 10% to 90% rise time of about 25 milliseconds with a settling time of about 0.17 seconds when 26 N and 78 N forces are exerted on the control unit connected thereto.

17. The system of claim 12, wherein said pressurized fluid-filled tubes are filled with a pressurized fluid of at least 0.1 MPa when said system has to generate an output torque of about 0.49 Nm or more.

18. The system of claim 1 is used to control or being installed in various MRI-guided robotic platforms for actuation, wherein the platforms are for at least one of endovascular procedures, neurosurgery, prostate surgery, and breast biopsy.

19. The system of claim 1, wherein said control and slave units comprise three piston and cylinder units arranged parallel to output axis of the rotary motion and evenly spaced about the output axis.

20. The system of claim 1, wherein said control and slave units comprise three piston and cylinder units arranged parallel to each other and perpendicular to the output shaft.

* * * * *